United States Patent
Koltz, Jr.

(10) Patent No.: US 12,403,271 B2
(45) Date of Patent: Sep. 2, 2025

(54) VANE COMPRESSOR FOR SURGICAL GAS DELIVERY SYSTEM WITH GAS SEALED INSUFFLATION AND RECIRCULATION

(71) Applicant: Conmed Corporation, Utica, NY (US)

(72) Inventor: Michael Koltz, Jr., Aurora, CO (US)

(73) Assignee: Conmed Corporation, Largo, FL (US)

(*) Notice: Subject to any disclaimer, the term of this patent is extended or adjusted under 35 U.S.C. 154(b) by 331 days.

(21) Appl. No.: 17/177,429

(22) Filed: Feb. 17, 2021

(65) Prior Publication Data

US 2022/0233792 A1   Jul. 28, 2022

Related U.S. Application Data

(63) Continuation-in-part of application No. 17/155,572, filed on Jan. 22, 2021, now Pat. No. 12,053,572, and a continuation-in-part of application No. 17/155,478, filed on Jan. 22, 2021.

(51) Int. Cl.
A61M 13/00     (2006.01)

(52) U.S. Cl.
CPC ..... *A61M 13/006* (2014.02); *A61M 2205/103* (2013.01); *A61M 2205/3365* (2013.01); *A61M 2205/8275* (2013.01)

(58) Field of Classification Search
CPC .......... A61M 13/006; A61M 2205/103; A61M 2205/3365; A61M 2205/8275; A61M 13/00; A61M 13/003; A61M 16/0063; A61M 60/806; A61M 2205/10; A61B 17/3423; F04C 18/3441; F04C 18/344; F04C 2/344
See application file for complete search history.

(56) References Cited

U.S. PATENT DOCUMENTS

| | | | |
|---|---|---|---|
| 4,930,997 A * | 6/1990 | Bennett | A61M 1/84 604/319 |
| 6,220,245 B1 * | 4/2001 | Takabayashi | A61M 16/0057 128/202.13 |
| 7,854,724 B2 | 12/2010 | Stearns et al. | |
| 8,795,223 B2 | 8/2014 | Stearns et al. | |
| 9,199,047 B2 | 12/2015 | Stearns et al. | |
| 9,375,539 B2 | 6/2016 | Stearns et al. | |

(Continued)

FOREIGN PATENT DOCUMENTS

| EP | 0058456 A1 | 8/1982 |
|---|---|---|
| JP | H10068390 A | 3/1998 |

(Continued)

OTHER PUBLICATIONS

PCT International Search Report and Written Opinion dated Jun. 22, 2022, issued during the prosecution of PCT International Publication No. PCT/US2022/012958.

*Primary Examiner* — Kami A Bosworth
*Assistant Examiner* — Avery Smale
(74) *Attorney, Agent, or Firm* — Troutman Pepper Locke LLP; Scott D. Wofsy

(57) ABSTRACT

A vane compressor for a surgical gas delivery system is disclosed, which includes a compressor head having an outlet port for delivering pressurized gas to a gaseous sealing manifold communicating with a gas sealed trocar and an inlet port for receiving spent gas from the gaseous sealing manifold by way of the gas sealed trocar, wherein the compressor head is coupled to and driven by a motor.

7 Claims, 3 Drawing Sheets

(56) References Cited

U.S. PATENT DOCUMENTS

| | | | |
|---|---|---|---|
| 10,702,306 B2 | 7/2020 | Silver et al. | |
| 2008/0044300 A1* | 2/2008 | Sakuda | F01C 21/02 |
| | | | 417/410.3 |
| 2015/0064042 A1* | 3/2015 | Shimaguchi | F04C 28/10 |
| | | | 418/259 |
| 2017/0000959 A1* | 1/2017 | Mantell | A61M 13/003 |
| 2018/0296245 A1* | 10/2018 | Stearns | A61B 17/3474 |
| 2019/0150981 A1 | 5/2019 | Silver et al. | |

FOREIGN PATENT DOCUMENTS

| | | |
|---|---|---|
| KR | 10-2009-0104151 A | 10/2009 |
| WO | 2015174861 A1 | 11/2015 |

* cited by examiner

VANE COMPRESSOR FOR SURGICAL GAS DELIVERY SYSTEM WITH GAS SEALED INSUFFLATION AND RECIRCULATION

CROSS-REFERENCE TO RELATED APPLICATIONS

The subject application is a continuation-in-part of U.S. application Ser. No. 17/155,478 filed Jan. 22, 2021, and a continuation-in-part of U.S. application Ser. No. 17/155,572 filed Jan. 22, 2021, the disclosures of which are both herein incorporated by reference in their entireties.

BACKGROUND OF THE INVENTION

1. Field of the Invention

The subject invention is directed to endoscopic surgery, and more particularly, to a surgical gas delivery system for gas sealed insufflation and recirculation that has a vane compressor coupled to a direct current motor for use during an endoscopic or laparoscopic surgical procedure.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the cavity, so that a surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. Nos. 7,854,724 and 8,795,223. These access devices are constructed from several nested components including an inner tubular body portion and a coaxial outer tubular body portion. The inner tubular body portion defines a gas sealed central lumen for introducing conventional laparoscopic or endoscopic surgical instruments to the surgical cavity of a patient and the outer tubular body portion defines an annular lumen surrounding the inner tubular body portion for delivering insufflation gas to the surgical cavity of the patient and for facilitating periodic sensing of abdominal pressure.

SurgiQuest has also developed multimodal surgical gas delivery systems for use with the unique gas sealed access devices described above. These gas delivery systems, which are disclosed for example in U.S. Pat. Nos. 9,199,047 and 9,375,539 have a first mode of operation for providing gas sealed access to a body cavity, a second mode of operation for performing smoke evacuation from the body cavity, and a third mode of operation for providing insufflation gas to the body cavity. The first and second modes utilize a recirculating gas flow that is pressurized by a relatively large and heavy piston-type compressor that is driven by an AC motor at speeds up to 3600 rpm. Although, commonly assigned U.S. Pat. No. 10,702,306 describes a similar gas delivery system where a DC motor is coupled to a compressor head.

Small diameter electric motors inherently exhibit less unbalance than larger motors due to their lower rotating inertia. This enables a small diameter electric motor to operate at substantially higher speeds than larger diameter motors without exhibiting audible noise and shorter bearing life. When used as a positive displacement compressor or pump driver, small diameter motors yield higher revolutions per given unit of time, reducing the required volumetric displacement per revolution of the compressor or pump head to produce an equivalent flow rate.

For example, a prior art motor operating at 1800 rpm and coupled to a two piston pump produces a total flow rate of 45 slpm, equating to a volumetric displacement of 25 cc/rev. In contrast, a motor operating at 18,000 rpm coupled to a vane pump producing 45 slpm of flow, equates to a volumetric displacement of 2.5 cc/rev. This displacement is one-tenth that of the prior example, and can be assumed to translate into a compressor having dimensions of the cube root of one-tenth of the prior example. Or in other words, at ten times the motor speed, the compressor length, height, and width would be about 46% of the dimension of the lower speed motor.

Additionally, the smaller size of the motor and head have a smaller surface area, reducing the amount of ambient air displaced through surface vibration. This will result in less audible noise that is often distracting to operating room staff. Also, the smaller mass of the reciprocating vanes compared to reciprocating pistons in the prior art pump produces less vibration and therefore less noise.

Furthermore, the higher rotational speeds and vane counts produce a high frequency noise in the range of 1 to 2 kHz, which is much higher than the primary mode noise produced by a piston pump, which is typically at a frequency of 150 Hz. Equipment producing noise in the range of 100 to 400 Hz is generally perceived to be distracting and of low noise quality. Applying this concept to the example above, an 1800 rpm motor driving a two piston pump would likely produce a noise frequency of 60 Hz (1800 rpm*1 min/60 sec*2 pistons). Comparatively, an 18,000 rpm motor driving a six vane pump would likely produce a noise frequency of 1800 Hz (18,000 rpm*1 min/sec*6 vanes).

It would be beneficial therefore to incorporate a motor driven vane compressor into a gas delivery system used during an endoscopic or laparoscopic surgical procedure, so as to reduce the size and weight of the system, and thereby improve operating room workflow and reduce the incidence of staff injury.

SUMMARY OF THE DISCLOSURE

The subject invention is directed to a new and useful vane compressor assembly for a surgical gas delivery system that includes a compressor head having an outlet port for delivering pressurized gas to a gaseous sealing manifold communicating with a gas sealed trocar and an inlet port for receiving spent gas from the gaseous sealing manifold by way of the gas sealed trocar. The compressor head is coupled to and driven by a motor. The motor can be a direct current (DC) motor or an alternating current (AC) motor, but a DC motor will be relatively smaller and lighter than an AC motor, and therefore more advantageous from a manufacturing standpoint.

A pump body is operatively associated with the compressor head and it defines a cylindrical bore having a central axis. A hub is mounted for rotation within the cylindrical bore of the pump body about a shaft defining an axis of rotation of the hub. The axis of rotation of the hub is offset from a central axis of the cylindrical bore, and the hub contains a plurality of circumferentially spaced apart vane slots each containing a freely sliding vane.

Each end of the shaft is supported in the pump body by a bearing and a mechanical shaft seal dynamically seals a gap between the shaft and the compressor head. An inlet conduit connects the inlet port to an inlet recessed surface and an outlet conduit connects the outlet port to an outlet recessed surface, and wherein the inlet and outlet recessed surfaces are disposed about the central axis of the pump body with the inlet recess terminating at about the point where a gap between the hub and the pump body is greatest, and the outlet recess terminating at about the point where the gap between the hub and the pump body is least.

The vane compressor assembly has a nominal volumetric displacement ranging from 0.1 to 10 cc/rev, and preferably the nominal volumetric displacement is about 2 cc/rev. The vane compressor assembly has a nominal speed ranging from 5,000 to 100,000 rpm, and preferably the nominal speed is about 20,000 rpms. The hub of the compressor head has between three and twelve vanes each freely sliding within a corresponding slot, and preferably there are six vanes each freely sliding within a corresponding slots.

The subject invention is also directed to a surgical gas delivery system for gas sealed insufflation and recirculation, which includes a gaseous sealing manifold for communicating with a gas sealed access port, an insufflation manifold for communicating with the gas sealed access port and with a valve sealed access port, a positive displacement rotary vane compressor for recirculating gas through the gas sealed access port by way of the gaseous sealing manifold, and a direct current motor coupled to the vane compressor.

These and other features of the vane compressor of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the vane compressor of the subject invention without undue experimentation, preferred embodiments thereof will be described in detail herein below with reference to the figures wherein.

DETAILED DESCRIPTION OF THE PREFERRED EMBODIMENTS

Figure 1:
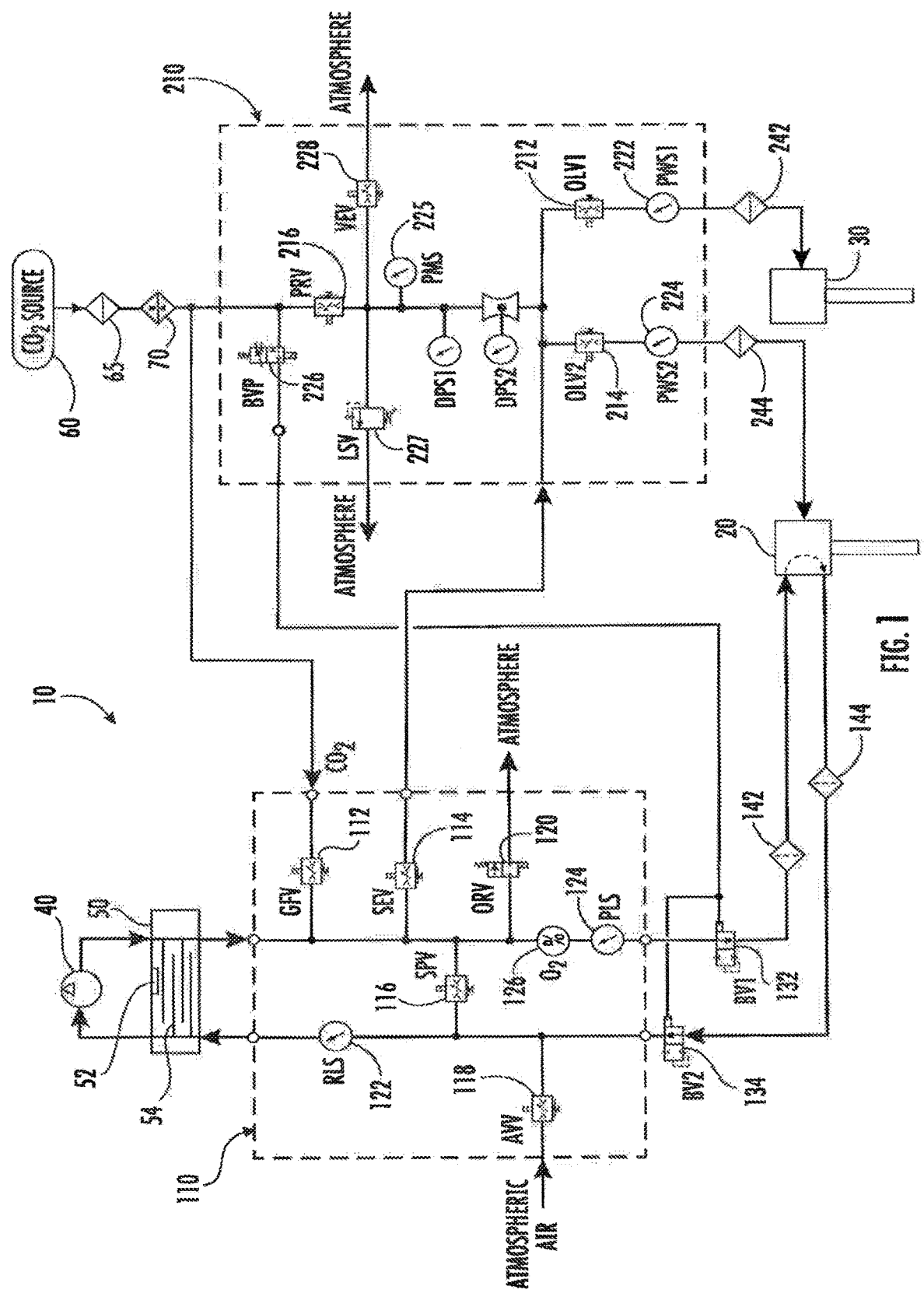
FIG. 1 is a schematic diagram of the multi-modal gas delivery system of the subject invention, which includes a gaseous sealing manifold for communicating with a gas sealed access port and an insufflation manifold for communicating with the gas sealed access port and with a valve sealed access port, wherein the gas delivery system includes a vane compressor assembly.

Referring now to the drawings wherein like reference numerals identify similar structural elements and features of the subject invention, there is illustrated in FIG. 1 a new and useful multi-modal surgical gas delivery system 10 that is adapted and configured for gas sealed insufflation, recirculation and smoke evacuation during an endoscopic or laparoscopic surgical procedure. The multi-modal surgical gas delivery system 10 of the subject invention includes a gaseous sealing manifold 110 for communicating with a gas sealed access port 20 and an insufflation manifold 210 for communicating with the gas sealed access port 20 and with a valve sealed access port 30.

The gas sealed access port 20 is of the type disclosed in commonly assigned U.S. Pat. No. 8,795,223, which is incorporated herein by reference. The gas sealed access port 20 is adapted and configured to provide gas sealed instrument access to a body cavity, while maintaining a stable pressure within the body cavity (e.g., a stable pneumoperitoneum in the peritoneal or abdominal cavity). In contrast, the valve sealed access port 30 is a conventional or standard trocar, for providing access to a body cavity through a mechanical valve seal, such as, for example, a duckbill seal, septum seal or the like. Depending upon the requirements of a particular surgical procedure, the multi-modal gas delivery system 10 can be utilized with either the gas sealed access port 20, the valve sealed access port 30 or with both access ports 20, 30 at the same time.

The gas delivery system 10 further includes a compressor assembly or positive displacement pressure pump 40 for recirculating surgical gas through the gas sealed access port 20 by way of the gaseous sealing manifold 110. The compressor 40 is preferably driven by a brushless DC (direct-current) motor, which can be advantageously controlled to adjust gas pressure and flow rates within the gas delivery system 10. Alternatively, the compressor 40 can be driven by an AC motor, but a DC motor will be relatively smaller and lighter, and therefore more advantageous from a manufacturing standpoint. A preferred embodiment of a positive displacement rotary vane compressor coupled to a direct current motor is described in greater detail below with reference to FIGS. 2 through 5.

An intercooler and/or condenser 50 is operatively associated with the compressor 40 for cooling or otherwise conditioning gas recirculating through the gaseous sealing manifold 110. A UVC irradiator 52 is operatively associated with the intercooler or condenser 50 for sterilizing gas recirculating through the internal flow passages 54 formed therein by way of the compressor 40. In addition, the UVC irradiator is intended to sterilize the interior surfaces of the gas conduits or flow passages through which the gas flows within the intercooler/condenser 50.

The UVC irradiator 52 preferably includes at least one LED light source or a florescent light source that is adapted and configured to generate UVC radiation at a wavelength of about between 240-350 nm, and preferably about 265 nm. This ultraviolet light at such a wavelength can sterilize viral, bacterial and microbial bodies within the gas conduits of the system, and can reduce coronavirus including SARS-COV-2.

Preferably, compressor assembly 40, intercooler/condenser 50, gaseous sealing manifold 110 and insufflation manifold 210 are all enclosed within a common housing, which includes a graphical user interface and control electronics, as disclosed for example in commonly assigned U.S. Pat. No. 9,199,047, which is incorporated herein by reference.

The gas delivery system 10 further includes a surgical gas source 60 that communicates with the gaseous sealing manifold 110 and the insufflation manifold 210. The gas source 60 can be a local pressure vessel or a remote supply tank associated with a hospital or healthcare facility. Preferably, gas from the surgical gas source 60 flows through a high pressure regulator 65 and a gas heater 70 before it is delivered to the gaseous sealing manifold 110 and the insufflation manifold 210. Preferably, the high pressure regulator 65 and the gas heater 70 are also enclosed with the compressor 40, intercooler 50, gaseous sealing manifold 110 and insufflation manifold 210 in the common housing.

The gas delivery system 10 further includes a first outlet line valve (OLV1) 212 that is operatively associated with the insufflation manifold 210 for controlling a flow of insufflation gas to the valve sealed access port 30 and a second outlet line valve (OLV2) 214 that is operatively associated with the insufflation manifold 210 for controlling a flow of insufflation gas to the gas sealed access port 20.

In accordance with a preferred embodiment of the subject invention, the first and second outlet line valves 212, 214 of insufflation manifold 210 are proportional valves that are configured to dynamically alter or otherwise control the outflow of insufflation gas to the access ports 20, 30 to match volume fluctuations that may arise in a patient's body cavity as they occur. The first and second proportional outlet line valves 212, 214 provide the gas delivery system 10 with fine control of insufflation gas flow rate to achieve stable flow rates at lower pressure, reduce pressure oscillation and eliminate pneumatic hammer.

Because the first and second proportional outlet line valves 212, 214 are proximal to the patient where flow friction losses are relatively low, the gas delivery system 10 is able to measure peritoneal pressures accurately. Moreover, the use of proportional outlet line valves for this purpose is uniquely possible here, because there is constant gas recirculation throughout the gas delivery system 10, either by way of closed loop smoke evacuation or by way of the gas sealed access port 20.

Proportional valves allow for infinitely variable gas flow adjustment between a minimum flow state and a maximum flow state. Given that some volume changes in a patient's body cavity, such as breathing, are expected and consistent, by employing proportional outlet line valves, the insufflation manifold 210 is able to dynamically alter the gas flow to the body cavity to inverse the expected volume changes, resulting in a neutral effect on the pressure inside the cavity.

An additional benefit of using proportional valves for controlling the outflow of insufflation gas from manifold 210 is a reduction in response time, as compared to that of a solenoid valve. A solenoid valve operates by applying energy to coils, which produces an electromagnetic force that moves a piston. However, the energizing of the coils takes some amount of time, introducing a delay between a commanded action and the physical movement of the piston. In contrast, proportional valves, as employed in the gas delivery system 10 of the subject invention, do not have an energization delay in general, and so they have an improved response time as compared to solenoid valves.

The insufflation manifold 210 further includes a first patient pressure sensor (PWS1) 222 downstream from the first outlet line valve 212 and a second patient pressure sensor (PWS1) 224 downstream from the second outlet line valve 214. These two patient pressure sensors are used to measure abdominal pressure to control outlet line valves 212, 214, respectively. Two other pressure sensors are located upstream from the outlet line valves 212, 214, and are labeled as DPS1 and DPS2. These two pressure sensors are situated within a venturi to measure a pressure differential that is used to infer a total gas flow rate from the insufflation manifold 210 to the patient's body cavity.

A primary proportional valve (PRV) 216 is also operatively associated with insufflation manifold 210 and it is located upstream from the first and second outlet line valves 212, 214 to control the flow of insufflation gas to the first and second outlet line valves 212, 214. Proportional valve 216 functions to maintain an intermediate pressure within the insufflation manifold 210 (as the central node in the LPU) at a constant pressure between 1 and 80 mmHg, dependent on the system operating mode. The opening of PRV 216 can be indirectly initiated by any of the following actions: patient respiration, gas leakage downstream of PRV 216, or the opening of the safety valve LSV 227 or ventilation valve VEV 228, i.e. any event that causes an intermediate pressure to drop. In the system. LSV 227 and VEV 228 are described in more detail below.

The gaseous sealing manifold 110 also includes a high pressure gas fill valve (GFV) 112 that is operatively associated with an outlet side of the compressor 40. GFV 112 is adapted and configured to control gas delivered into the gaseous sealing manifold 110 from the source of surgical gas 60. Preferably, the gas fill valve 112 is a proportional valve that is able to dynamically control surgical gas delivered into the gaseous sealing manifold 110.

The gaseous sealing manifold 110 also includes a smoke evacuation valve (SEV) 114 that is operatively associated with an outlet side of the compressor 40 for dynamically controlling gas flow between the gaseous sealing manifold 110 and the insufflation manifold 210 under certain operating conditions, such as, for example, when the gas delivery device 10 is operating in a smoke evacuation mode. Preferably, the smoke evacuation valve 114 is a proportional valve.

A bypass valve (SPV) 116 is positioned between an outlet side of the compressor 40 and an inlet side of the compressor 40 for controlling gas flow within the gaseous sealing manifold 110 under certain operating conditions. Preferably, the bypass valve 116 is a proportional valve, which is variably opened to establish and control the gaseous seal generated within gas sealed access port 20. Moreover, bypass valve 116 controls gas flow rate to the gaseous seal using feedback from pressure sensors 122, 124, described in further detail below.

The gaseous sealing manifold 110 also includes an air ventilation valve (AVV) 118, which is operatively associated with an inlet side of the compressor 40 for controlling the entrainment of atmospheric air into the system 10 under certain operating conditions. For example, AVV 118 will permit the introduction of atmospheric air into the gaseous sealing circuit to increase the air mass (i.e., the standard volume) within the circuit. The thermodynamics of clinical use conditions can cause a loss of standard volume within the gas circuit. The ventilation valve 118 permits the gas delivery system 10 to make up for this lost volume, in order to ensure that pump pressure and flow rates are sufficient to maintain the gaseous seal within the gas sealed access port 20. The ventilation valve 118 can also be opened to reduce the vacuum side pressure in the gas seal circuit.

An overpressure relief valve (ORV) 120 is operatively associated with an outlet side of the compressor 40 for controlling a release of gas from the system 10 to atmosphere under certain operating conditions. Preferably, the overpressure relief valve 120 is a proportional valve that is opened to reduce the positively pressurized side of the gas seal circuit, especially in the event of an emergency, such as a loss of power to the gas delivery system 10. The normally open configuration of relief valve 120 reduces the risk of over-pressurization of the patient cavity upon loss of power to that valve.

A first pressure sensor (RLS) 122 is operatively associated with an inlet side of the compressor 40 and a second pressure sensor (PLS) 124 is operatively associated with an outlet side of the compressor 40. These pressure sensors 122, 124 are situated to have unobstructed and minimally restricted commutation with the patient's abdominal cavity in order to continuously and accurately measure cavity pressure. The signals from these two pressure sensors 122, 124 are employed by a controller of the gas delivery system 10 to modulate the opening of the two outlet line valves 212 and 214, to control the patient cavity pressure.

In addition, the gaseous sealing manifold 110 includes a gas quality sensor 126 that is operatively associated with an outlet side of the compressor 40. The gas quality sensor monitors the level of oxygen in the recirculation circuit, which corresponds to a concentration of $CO_2$ in the body cavity of a patient, as disclosed in U.S. Pat. No. 9,199,047.

A first blocking valve (BV1) 132 is operatively associated with an outlet flow path of the gaseous sealing manifold 110 and a second blocking valve (BV2) 134 is operatively associated with an inlet flow path to the gaseous sealing manifold 110. The blocking valves 132, 134 are employed during a self-test prior to a surgical procedure, as disclosed in U.S. Pat. No. 9,199,047. It is envisioned that the first and second blocking valves 132, 134 could be are mechanically actuated or pneumatically actuated.

A first filter element 142 is positioned downstream from the first blocking valve 132 for filtering pressurized gas flowing from the compressor 40 to the gas sealed access port 20, and a second filter element 144 is positioned upstream from the second first blocking valve 134 for filtering gas returning to the compressor 40 from the gas sealed access port 20. Preferably, the filter elements 142, 144 are housed within a common filter cartridge, as disclosed for example in U.S. Pat. No. 9,199,047.

The first and second blocking valves 132, 134 communicate with a blocking valve pilot (BVP) 226 that is included within with the insufflation manifold 210. Preferably, the blocking valve pilot 226 is a solenoid valve. It is envisioned that BVP 226 could be fed from the compressor outlet as shown or from a gas source such of surgical gas or air. The insufflation manifold 110 further includes a pressure sensor (PMS) 225 located downstream from the primary proportional valve 216 and upstream from the outlet line valves 212, 214. The two outlet line valves are opened to introduce insufflation gas to the patient's body cavity by way of the access ports 23, 30. This introduction of gas has the effect of increasing pressure within the body cavity. Additionally, the outlet line valves 212, 214 can be opened in conjunction with air ventilation valve 228 to release gas from the body cavity, having the effect of desufflation and reduction of cavity pressure.

The insufflation manifold 210 further includes a low pressure safety valve (LSV) 227 downstream from the primary proportional valve 216 and upstream from the first and second outlet line valves 212, 214 for controlling a release of gas from the system 10 to atmosphere under certain operating conditions. LSV 227 is a purely mechanical valve that functions to limit the maximum intermediate pressure within the manifold 210 or LPU (Low Pressure Unit) in the event of a power interruption, a pressure controller malfunction or if a valve located upstream from the LSV sticks in an open position.

In addition, a ventilation exhaust valve (VEV) 228 is positioned downstream from the primary proportional valve 216 and upstream from the outlet line valves 212, 214 for controlling a release of gas from the system 10 to atmosphere under certain operating conditions. The ventilation exhaust valve 228 is a preferably a proportional valve that is opened to de-sufflate or otherwise reduce patient cavity pressure. Additionally, VEV 228 can be opened to reduce intermediate pressure within the LPU.

A filter element 242 is positioned downstream from the first outlet line valve 212 for filtering insufflation gas flowing from the insufflation manifold 210 to the valve sealed access port 30. Another filter element 244 is positioned downstream from the second outlet line valve 224 for filtering insulation gas flowing from the insufflation manifold 210 to the gas sealed access port 20. Preferably, filter element 244 is housed with filter elements 142 and 144 in a common filter cartridge, while filter element 242 is separately located.

Figure 2:
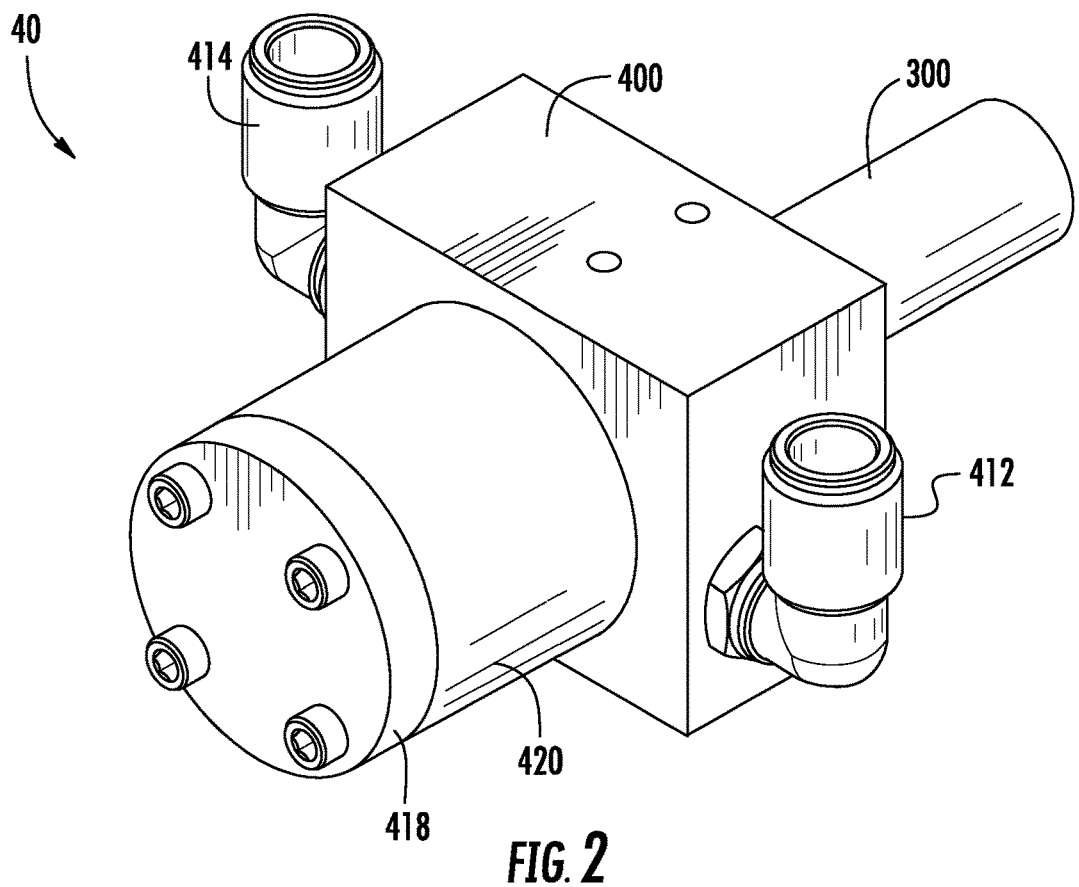
FIG. 2 is a perspective view of the vane compressor assembly employed in the gas delivery system of FIG. 1, which includes a compressor head coupled to a direct current motor.

Referring now to FIG. 2, there is illustrated the positive displacement rotary vane compressor assembly 40 of the subject invention. The compressor assembly 40 includes a direct current (DC) motor 300 that is directly coupled to a compressor head 400. Alternatively, an alternating current (AC) motor could be coupled to the compressor head 400, but a DC motor will be relatively smaller and lighter than an AC motor, and therefore more advantageous from a manufacturing standpoint. In either case, the motor 300 is driven by an electrical controller. During operation, gas is induced into compressor head 400 through an inlet port 412 and discharged through an outlet port 414. More particularly, the outlet port 414 delivers pressurized gas to the gaseous sealing manifold 110 which communicates with the gas sealed trocar 20 and the inlet port 412 receives spent gas from the gaseous sealing manifold 110 by way of the gas sealed trocar 20, as best seen in FIG. 1.

In accordance with the subject invention, the compressor assembly 40 has a nominal volumetric displacement ranging from 0.1 to 10 cc/rev and preferably the nominal volumetric displacement of the compressor assembly 40 is about 2 cc/rev. The compressor assembly 40 rotates at a nominal radial speed ranging from 5,000 to 100,000 rpm and preferably the nominal radial speed of the compressor assembly 40 is about 20,000 rpm.

Figure 3:
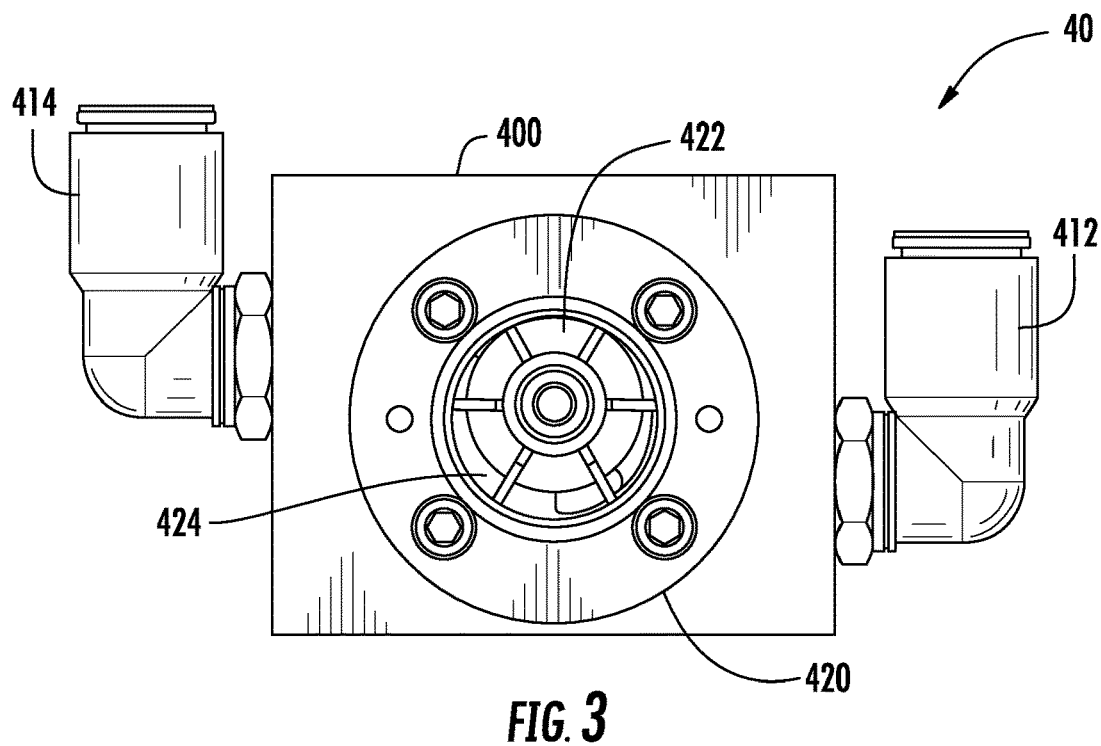
FIG. 3 is a front elevational view of the vane compressor assembly with the end cap removed to show the hub housed within the cylindrical bore of the pump body.

Referring now to FIG. 3, there is illustrated an end view of the compressor assembly 40 with the end cap 418 of the pump body 420 removed to show the hub 422 of the compressor assembly 40 situated therein. More particularly, the hub 422 rotates within a cylindrical bore 424 of the pump body 420. The axis of rotation of the hub 422 is offset from the cylindrical bore 424 of the pump body 420.

Figure 4:
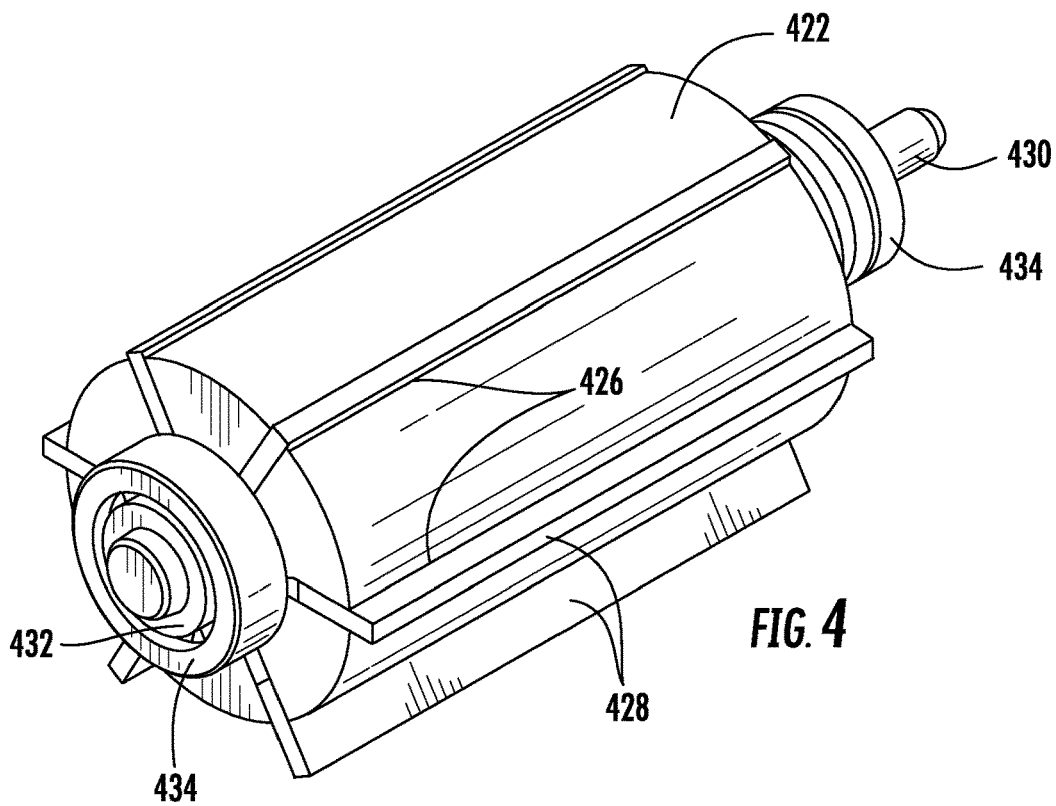
FIG. 4 is a perspective view of the rotating hub assembly shown with six circumferentially spaced apart vanes.

Referring to FIG. 4, the hub 422 contains a plurality of equally spaced slots 426 in which respective vanes 428 are free to slide. The nominal design of the compressor assembly 40 of the subject invention employs six vanes 428 sliding within six respective slots 426 of a common hub 422, although other embodiments of the compressor assembly 40 may include between 3 and 12 vanes inclusively.

The vane slots 426 need not radially intersect the axis of the hub 422, instead they may be offset from the axis of the hub 422. Centripetal force due to the rotation of the hub 422 keeps each vane in contact with the interior wall of the cylindrical bore 424 of pump body 420 forming a dynamic seal therebetween. As the hub 422 rotates and the vanes 428 maintain contact with the interior wall of the bore 424, the sealed volume between each adjacent pair of vanes 428 changes. During one half of the rotation, volume is increasing and drawing gas in through the inlet port 412, and during the other half of the rotation, the volume is decreasing and compressing gas and moving it out of the outlet port 414.

With continuing reference to FIG. 4, the hub 422 is connected to and rotates with an elongated shaft 430. Each end of the shaft 430 is supported by a bearing 432. A mechanical shaft seal 434 dynamically seals the gap between the shaft 430 and the compressor head 400.

Figure 5:
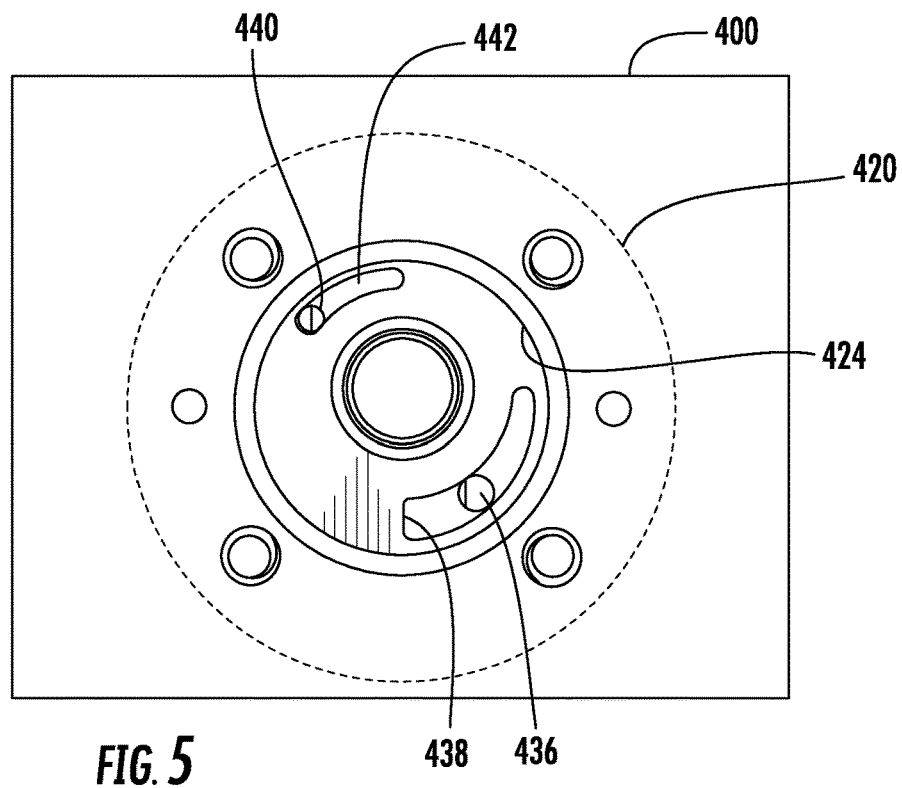
FIG. 5 is a cross-sectional view of the compressor head showing details of the internal porting.

Referring now to FIG. 5, there is shown the internal porting features of the pump body 420. More particularly, an inlet conduit 436 connects the inlet port 412 to an inlet recessed surface 438. Similarly, an outlet conduit 440 connects the outlet port 414 to an outlet recessed surface 442. The recessed surfaces 438, 442 are disposed about the central axis of the cylindrical bore 424 of pump housing 420 with the inlet recess 438 terminating at about the point where the gap between the hub 422 and the pump body 420 is greatest, and the outlet recess 442 terminating at about the point where the gap between the hub 422 and the pump body 420 is least.

While the vane compressor assembly and gas delivery system of the subject disclosure has been shown and described with reference to preferred embodiments, those skilled in the art will readily appreciate that changes and/or modifications may be made thereto without departing from the scope of the subject disclosure.

What is claimed is:

1. A surgical gas delivery system comprising:
 a) a manifold for communicating with a gas sealed access port;
 b) a proportional fill valve for dynamically controlling delivery of a gas into the manifold from a gas source;
 c) a positive displacement rotary vane compressor assembly for recirculating the gas through the gas sealed access port by way of the manifold, the positive displacement rotary vane compressor assembly including a compressor head having an inlet port on a first side surface of the compressor head for receiving a spent gas flow from the gas sealed access port through the manifold and an outlet port on a second side surface of the compressor head for discharging a pressurized gas flow to the gas sealed access port through the manifold;
 d) a pump body extending from a front surface of the compressor head;
 e) a brushless direct current motor coupled to a rear surface of the compressor head for driving the positive displacement rotary vane compressor assembly; and
 f) an intercooler and/or a condenser interposed between the manifold and the positive displacement rotary vane compressor assembly for conditioning the spent gas flow received by the positive displacement rotary vane compressor assembly from the manifold and for conditioning the pressurized gas flow discharged from the positive displacement rotary vane compressor assembly to the manifold,
 wherein the spent gas flow travels directly from an outlet of the manifold to a first inlet of the intercooler and/or the condenser and then from a first outlet of the intercooler and/or the condenser to the inlet port of the compressor head, and the pressurized gas flow travels directly from the outlet port of the compressor head to a second inlet of the intercooler and/or the condenser and then from a second outlet of the intercooler and/or the condenser to an inlet of the manifold.

2. The surgical gas delivery system as recited in claim 1, wherein the pump body defines a cylindrical bore, and a hub is mounted for rotation within the cylindrical bore of the pump body about a shaft that defines an axis of rotation of the hub, and wherein the axis of rotation of the hub is offset from a central axis of the cylindrical bore, and wherein the hub contains a plurality of circumferentially spaced apart vane slots each containing a freely sliding vane.

3. The surgical gas delivery system as recited in claim 2, wherein each end of the shaft is supported within the pump body by a bearing, and a mechanical shaft seal dynamically seals a gap between the shaft and the compressor head.

4. The surgical gas delivery system as recited in claim 1, wherein the positive displacement rotary vane compressor assembly has a nominal volumetric displacement ranging from 0.1 to 10 cc/rev.

5. The surgical gas delivery system as recited in claim 1, wherein the positive displacement rotary vane compressor assembly has a nominal volumetric displacement of about 2 cc/rev.

6. The surgical gas delivery system as recited in claim 1, wherein the positive displacement rotary vane compressor assembly has a nominal speed ranging from 5,000 to 100,000 rpm.

7. The surgical gas delivery system as recited in claim 1, wherein the positive displacement rotary vane compressor assembly has a nominal speed of about 20,000 rpms.

* * * * *